Figure 1:
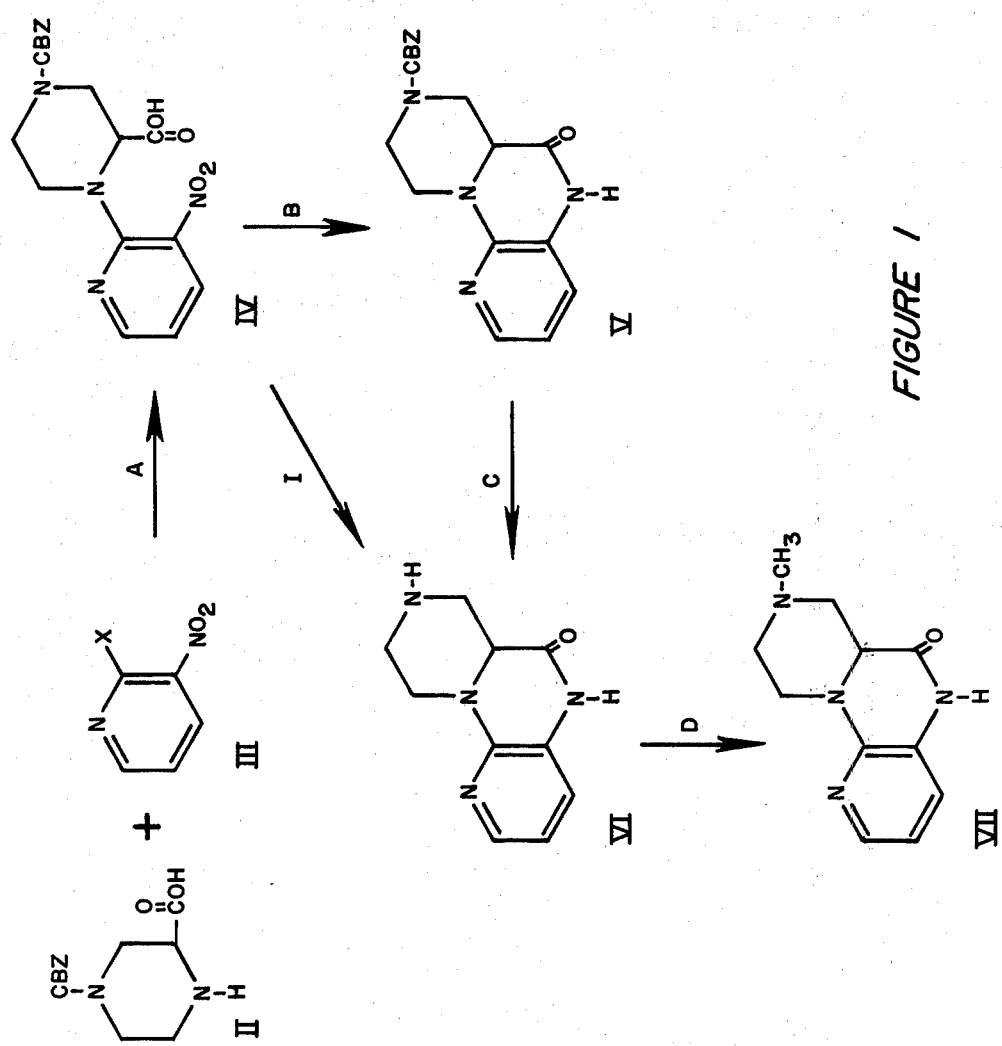

United States Patent [19]
Freed et al.

[11] 4,138,564
[45] Feb. 6, 1979

[54] TETRAHYDRO[1H]PYRAZINO[1,2-a]AZAQUINOXALIN-5(6H)-ONES AND DERIVATIVES THEREOF

[75] Inventors: Meier E. Freed, Paoli; John R. Potoski, Spring City, both of Pa.

[73] Assignee: American Home Products Corporation, New York, N.Y.

[21] Appl. No.: 821,381

[22] Filed: Aug. 3, 1977

[51] Int. Cl.² .......................................... C07D 471/14
[52] U.S. Cl. ..................................... 544/346; 424/250
[58] Field of Search .................. 260/268.7 R; 544/346

[56] References Cited
PUBLICATIONS
Winterfeld et al., Chem. Abst. 73, 35330s (1970).

Primary Examiner—Paul M. Coughlan, Jr.
Assistant Examiner—D. B. Springer

[57] ABSTRACT

Compounds of the formula

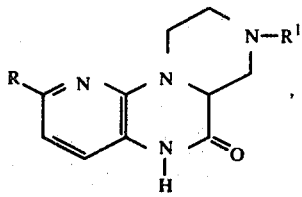

Ia

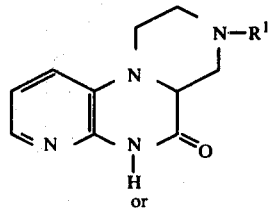

Ib or

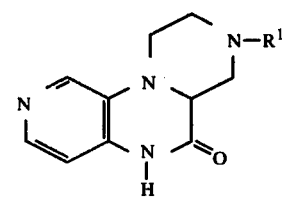

Ic wherein
R is hydrogen, chlorine, or fluorine; and
R¹ is hydrogen, methyl, ethyl, propyl, or isopropyl;
or a non-toxic acid addition salt thereof; exert an antihypertensive effect.

6 Claims, 1 Drawing Figure

TETRAHYDRO[1H]PYRAZINO[1,2-a]AZAQUINOXALIN-5(6H)-ONES AND DERIVATIVES THEREOF

The present invention relates to substituted 7,8,9,10-tetrahydro-5H-pyrazino[1,2-a]pyrido[3,2-e]pyrazin-6(6aH)-ones, 7,8,9,10-tetrahydro-5H-pyrazino[1,2-a]pyrido[4,3-e]pyrazin-6(6aH)-ones, and 2,3,4,4a-tetrahydro-1H-pyrazino[1,2-a]pyrido[2,3-e]-pyrazin-5(6aH)-ones, which compounds have pharmacological activity. Also contemplated by this invention are intermediates used in the synthesis of said compounds, pharmaceutical compositions containing said compounds, and methods of using said compounds.

The invention sought to be patented comprises chemical compounds of the formula:

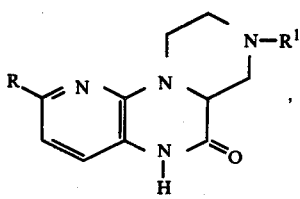

Ia

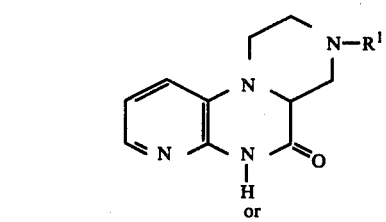

Ib or

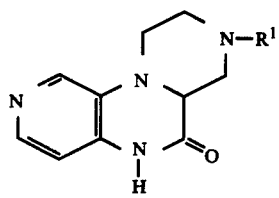

Ic wherein:
R is hydrogen, chlorine, or fluorine; and
R¹ is hydrogen, methyl, ethyl, propyl, or isopropyl;
or a non-toxic acid addition salt thereof.

The compounds of Formula Ia, Ib, or Ic, wherein R and R¹ have the meanings above-defined, and the non-toxic acid addition salts thereof, exert a hypotensive effect in hypertensive warm-blooded animals, as evidenced by pharmacological evaluation in standard test procedures.

Preferred compounds of Formula Ia, Ib, or Ic are those in which R and R¹, are each hydrogen. When R is a group other than hydrogen, fluorine is preferred.

Also within the scope of this invention are the intermediates employed in the synthesis of the compounds of Formula Ia, Ib, or Ic. Such intermediates are:

(a) compounds of the formula:

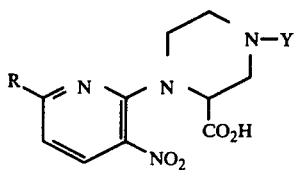

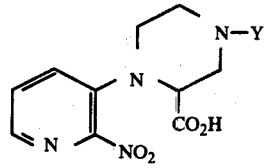

or

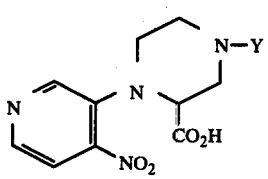

wherein:
Y is methyl, ethyl, propyl, isopropyl, or a protecting group for a secondary amine; and
R is hydrogen, chlorine, or fluorine;
or an N-oxide or a salt thereof; and (b) compounds of the formula:

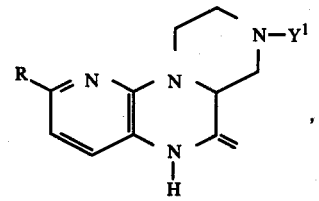

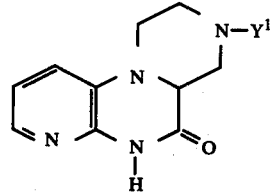

or

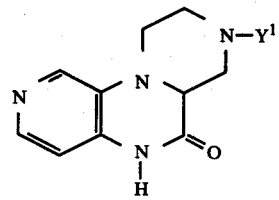

wherein:
Y¹ is a protecting group for a secondary amine; and
R is hydrogen, chlorine, or fluorine.

As used herein the term "protecting group for a secondary amine" is meant a group which will prevent undesirable side reactions at the secondary amine nitrogen during reactions leading to the final products, but will be easily removed by chemical means, when desired, to obtain the final products. Such protecting groups are conventional in the art of chemistry. Examples are: carbobenzoxy, benzhydryl, benzyl, trifluoroacetyl, t-butyloxycarbonyl, or tosyl. The carbobenzoxy group is preferred.

The general method of synthesis of the compounds of Formula Ia, Ib, or Ic is illustrated schematically in FIG.

I of the annexed Drawing which depicts the preparation of 7,8,9,10-tetrahydro-5H-pyrazino[1,2-a]pyrido[3,2-e]pyrazin-6(6aH)-one and the methyl substituted derivative thereof. The method depicted in FIG. I employs intermediates in which the protecting group (Y or Y¹) for the secondary amine nitrogen is illustrated by the carbobenzoxy group (represented in FIG. I by the symbol CBZ) having the structure:

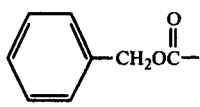

The symbol X in Formula III represents a chlorine, fluorine, or bromine atom.

Referring now to FIG. I, wherein the compounds are assigned Roman numerals for identification, in Process A, 4-carbobenzoxypiperazine-2-carboxylic acid (II) is condensed with a 2-halo-3-nitropyridine (III), to afford 4-carbobenzoxy-1-(3-nitro-2-pyridinyl)piperazine-2-carboxylic acid (IV). The reaction is carried out in an inert organic solvent, such as dimethylsulfoxide, dimethylformamide, or a water-(lower)alkanol solution, in the presence of a base, such as a teriary-alkyl amine (e.g. triethylamine) or an alkali metal carbonate or bicarbonate at a temperature from about 20° to about 100° C., preferably 60° C.

The intermediate IV is cyclized to 8-carbobenzoxy-7,8,9,10-tetrahydro-5H-pyrazino[1,2-a]pyrido[3,2-e]pyrazin-6(6aH)-one by a two-step process involving reduction of the nitro group to the amino group followed by cyclization. The reduction step is preferably performed by treating the nitro acid (IV) with a reducing agent, such as iron-acetic acid or sodium dithionite at a pH of 8–10. Other standard reagents capable of reducing an aromatic nitro group will be obvious to those skilled in the art. The amino acid thus produced is cyclized by adjusting the pH of the solution to about 7.5 or less (preferably a pH of about 3).

The 3-carbobenzoxy protecting group is removed from 8-carbobenzoxy-7,8,9,10-tetrahydro-5H-pyrazino[1,2-a]pyrido[3,2-e]-pyrazin-6(6aH)-one (V) by catalytic hydrogenation (Process C) to afford 7,8,9,10-tetrahydro-5H-pyrazino[1,2-a]pyrido[3,2-e]-pyrazin-6(6aH)-one (VI). The hydrogenation is carried out in an inert solvent, such as ethanol, in the presence of a catalyst, such as a noble metal (e.g. Raney nickel or palladium on carbon), at a pressure of from about 1 atm. to about 3 atm., preferably about 3 atom. If desired, the hydrogenation may be performed in the presence of an acid, such as hydrogen chloride which provides the product as the acid addition salt.

Catalytic hydrogenation (e.g. with Raney nickel) of the intermediate (IV) in the presence of an acid effects reduction, cyclization, and removal of the carbobenzoxy group and yields the product VI directly (Process I).

When it is desired to prepare the product containing a substituent at the 8-position, 7,8,9,10-tetrahydro-5H-pyrazino-[1,2-a]pyrido[3,2-e]pyrazin-6(6aH)-one (VI) is treated with a suitable alkylating agent (Process D), for example, an alkyl halide. The reaction is performed in an inert solvent, such as ethanol, preferably in the presence of a weak base, such as potassium carbonate. Other alkylating agents, such as the tosylate derivatives, will be apparent to those skilled in the art.

While the above method of synthesis has been described by reference to FIG. I which illustrates the preparation of 7,8,9,10-tetrahydro-5H-pyrazino[1,2-a]pyrido[3,2-e]pyrazin-6(6aH)-one (a compound of Formula Ia), it will be apparent to those skilled in the art of chemistry that the compounds of Formula Ib and Ic may be prepared by this method or by modifications of this method which would be obvious to those skilled in the art. Thus, compounds of Formula Ib and Ic may be prepared by employing an appropriate nitrohalopyridine in Process A and using the intermediates formed therefrom in the subsequent processes. For example; 7,8,9,10-tetrahydro-5H-pyrazino[1,2-a]pyrido[4,3-e]-pyrazin-6(6aH)-one can be prepared from a 3-halo-4-nitropyridine while 2,3,4,4a-tetrahydro-1H-pyrazino[1,2-a]pyrido[2,3-e]pyrazin-6(6aH)-one can be prepared from a 2-nitro-3-halopyridine.

The nitrohalopyridines employed as starting materials in the process described above are either known compounds or may be prepared from known compounds by methods which will be apparent to one skilled in the art of chemistry. The term "nitrohalopyridine" means a nitropyridine containing a fluorine, chlorine, or bromine atom in the appropriate position ortho to the nitro group. The nitrofluoropyridines are preferred starting materials since the fluorine atom is more easily replaced than chlorine or bromine. In some instances, it may be more convenient to use the N-oxide of the nitrohalopyridine, and for synthetic purposes such N-oxides are equivalent to the free base.

It will also be apparent that the nitrohalopyridine starting materials employed for preparing the compounds of Formula Ia can be further substituted with a chlorine or fluorine atom at a position ortho to the pyrido nitrogen, and such starting materials will afford the compounds of Formula Ia when R is chlorine or fluorine.

4-Carbobenzoxypiperazine-2-carboxylic acid (II) employed as a starting material in Process A is prepared from piperazine-2-carboxylic acid in three steps: (a) treating said acid, as the dihydrochloride, with cupric carbonate in water to form the cupric ion chelate; (b) treating the chelate with benzylchloroformate in acetone-water to introduce the carbobenzoxy group; and (c) treating the 3-carbobenzoxypiperazine-2-carboxylic acid, copper chelate with hydrochloric acid and hydrogen sulfide to destroy the chelate. The product is isolated as the hydrochloride salt. Other protected piperazine-2-carboxylic acids may be similarly prepared by treating the piperazine-2-carboxylic acid cupric ion chelate with a suitable blocking reagent to introduce the blocking group at the 4-position and then destroying the chelate.

In the method of synthesis depicted in FIG. 1, the carbobenzoxy group is employed as a blocking group to protect the reactive nitrogen of the piperazine ring of the intermediates. It will be obvious to those skilled in the art that any conventional blocking group useful for protecting a secondary amino group may be employed, for example; the benzhydryl, benzyl, trifluoroacetyl, t-butyloxycarbonyl, or tosyl group. Methods for removing a particular protecting group will be obvious to one skilled in the art of organic chemistry. For example a benzyl-type blocking group (e.g. a benzhydryl, benzyl, or carbobenzoxy group) can be removed by catalytic hydrogenation (hydrogenolysis). Hence, catalytically reducing an intermediate of Formula Ic containing the benzhydryl, benzyl, or carbobenzoxy group in the presence of an acid effects reduction, cyclization, and removal of the blocking group and provides a convenient method for preparing the compounds of Formula Ia wherein R and $R^1$ are hydrogen.

Certain blocking groups (e.g. carbobenzoxy, t-butyloxycarbonyl, trifluoroacetyl, or tosyl) can be removed by acid hydrolysis such as by treatment with hydrochloric acid.

The compounds of Formula Ia, Ib, or Ic, wherein R is methyl, ethyl, propyl, or isopropyl are conveniently prepared by an alternate process in which a 4-(lower)alkylpiperazine-2-carboxylic acid is employed in place of 4-carbobenzoxypiperazine-2-carboxylic acid (II) in Process A described above. Reduction of the nitro group of the product thus formed followed by cyclization (as in Process B, described above) directly gives the desired product without the need for blocking and deblocking the piperazine nitrogen.

Since the compounds of Formula Ia, Ib, or Ic possess an asymmetric carbon atom, optical enantiomorphs are possible, and the compounds of the invention may be in the form of the pure enantiomorph or mixtures thereof, such as the racemates.

The compounds of Formula Ia, Ib, or Ic may be obtained in the form of the pure enantiomorph either by resolving a desired racemic product or by resolving a racemic starting material or intermediate at any convenient stage of the synthesis. Methods of carrying out the resolution are well known in the art of chemistry. For example, the desired racemate may be treated with an optically active carboxylic acid and the optically active addition salts may be separated by standard techniques.

The compounds of Formula Ia, Ib, or Ic as obtained in the processes depicted in FIG. I, and the appropriate intermediates thereto, may be isolated and purified in a conventional manner. It is furthermore appreciated that in the various processes hereinbefore described, factors such as solvents or temperatures are not critical and the selection of a temperature or solvent for a particular process will be apparent to one skilled in the art.

The compounds of Formula Ia, Ib, or Ic may exist either in the form of the free base or the acid addition salt. Methods for converting one such form to another will be obvious to one skilled in the art of chemistry.

The amino acids, 4-(substituted)piperazine-2-carboxylic acid and the 4-(substituted)-1-(nitropyridinyl)-piperazine-2-carboxylic acids, employed as intermediates for preparing the compounds of Formula Ia, Ib, or Ic may exist either in the acid, base, or zwitterion form, and methods for converting one such form to another will be apparent to those skilled in the art.

For pharmacological use, the compounds of Formula Ia, Ib, or Ic may be administered in the form of an acid addition salt of a non-toxic organic or inorganic acid. The salts may be prepared by methods well known in the art. Appropriate salts are those formed from the following acids: hydrochloric, hydrobromic, sulfonic, sulfuric, phosporic, nitric, maleic, fumaric, benzoic, ascorbic, pamoic, succinic, methanesulfonic, acetic, propionic, tartaric, citric, lactic, malic, mandelic, cinnamic, palmitic, itaconic, and benzenesulfonic.

When employed to relieve hypertension, the effective dosage of the compounds of Formula Ia, Ib, or Ic will vary according to the particular compound being employed, the severity and nature of the hypertension, and the particular subject being treated. In general, with large warm-blooded animals (about 70 kg. body weight) effective results can be achieved by the oral route at a dosage level of from 25 mg. to about 2 g. given as needed, for example every four to six hours. A dose of about 25 mg. to about 500 mg. is preferred. Therapy should be initiated at lower dosages, the dosage thereafter being increased until the desired hypotensive effect is obtained.

When employed as hypotensive agents, the active substances of Formula Ia, Ib, or Ic may be administered alone or in combination with pharmaceutically acceptable carriers, the proportion and nature of which are determined by the solubility and chemical properties of the compound selected, the chosen route of administration, and standard pharmaceutical practice. For example, the compounds of Formula Ia, Ib, or Ic may be administered orally in solid dosage forms, e.g. capsules, tablets, or powders, or in liquid forms, e.g. solutions or suspensions. The compounds may also be injected parenterally in the form of sterile solutions or suspensions. Solid oral forms may contain conventional excipients, for instance: lactose, succrose, magnesium stearate, resins, and like materials. Liquid oral forms may contain various flavoring, coloring, preserving, stabilizing, solubilizing or suspending agents. Parenteral preparations are sterile aqueous or non-aqueous solutions or suspensions which may contain various preserving, stabilizing, buffering, solubilizing, or suspending agents. If desired, additives, such as saline or glucose may be added to make the solutions isotonic.

The following examples are illustrative of the processes of the invention. All temperatures are in centigrade.

EXAMPLE 1

1-(3-Nitro-2-pyridinyl)-4-carbobenzoxypiperazine-2-carboxylic acid

A solution of 6.0 g. of 4-carbobenzoxypiperazine-2-carboxylic acid hydrochloride, 3.3 g. of 2-chloro-3-nitropyridine and 15 ml. of triethyl amine in 100 ml. of dimethyl sulfoxide is heated at 60° with stirring for 18 hours. The mixture is diluted with 400 ml. of water, acidified to pH 3 with concentrated hydrochloric acid, and extracted repeatedly with ether. The combined ether extracts are dried ($MgSO_4$) and concentrated. The residue is crystallized from ethyl acetate/heptane to give 6.3 g. of the title product, m.p. 145°–147°.

Analysis for: $C_{18}H_{18}N_4O_6$; Calculated: C, 55.95; H, 4.70; N, 14.50; Found: C, 55.62; H, 4.68; N, 14.67.

EXAMPLE 2

1-(4-Nitro-3-pyridinyl, N-oxide)-4-carbobenzoxypiperazine-2-carboxylic acid

A mixture of 3.48 g. of 3-fluoro-4-nitropyridine-N-oxide, 6.6 g. of 4-carbobenzoxypiperazine-2-carboxylic acid hydrochloride, 15 ml. of triethylamine, and 100 ml. of methanol is stirred at room temperature for 18 hours. The solution is concentrated and the residue is dissolved in aqueous potassium bicarbonate solution. The pH is adjusted to 3 with aqueous hydrogen chloride then treated with methylene chloride and the resultant mixture is filtered to give 4.6 g. of the title product, m.p. 145° dec. Thin layer chromatographic analysis of this material shows one single spot.

Analysis for: $C_{18}N_{18}N_4O_7.1/2H_2O$; Calculated: C, 52.55; H, 4.65; N, 13.62; Found: C, 52.39; H, 4.48; N, 13.50.

EXAMPLE 3

1-(2-Nitro-3-pyridinyl)-4-carbobenzoxypiperazine-2-carboxylic acid

A mixture of 2.8 g. of 2-nitro-3-fluoropyridine, 5.0 g. of 4-carbobenzoxypiperazine-2-carboxylic acid, hydrochloride, 25 ml. of triethylamine, and 90 ml. of dimethyl sulfoxide is heated at 55° with stirring for 1½ hours, then allowed to stand at room temperature overnight. A similar workup to that described in Example 1 gives 4.5 g. of the title product as a viscous orange glass. Thin layer chromatographic analysis of this material shows one single spot.

EXAMPLE 4

1-(6-Fluoro-3-nitro-2-pyridinyl)-4-carbobenzoxypiperazine-2-carboxylic acid

In a similar procedure to that described in Example 1, from 6.0 g. of 2,6-difluoro-3-nitropyridine, 9.0 g. of 4-carbobenzoxypiperazine-2-carboxylic acid, hydrochloride, 20 ml. of triethylamine and 150 ml. of dimethyl sulfoxide, there is obtained 14 g. of the title product as a viscous orange glass. Thin layer chromatographic analysis of this material shows essentially one spot.

EXAMPLE 5

8-Carbobenzoxy-7,8,9,10-tetrahydro-5H-pyrazino[1,2-a]pyrido[3,2-e]pyrazino-6(6aH)-one A solution of 1.95 g. of 1-(3-nitro-2-pyridinyl-4-carbobenzoxypiperazine-2-carboxylic acid in 250 ml. of water is adjusted to pH 9-10 with aqueous sodium hydroxide. To this solution, with stirring, is added 3.5 g. of sodium dithionite in small portions. The pH is maintained between 8 and 10 by addition of small portions of aqueous sodium hydroxide while the dithionite is being added. After the addition of dithionite the pH of the solution is brought to 3 with concentrated hydrochloric acid, then is brought back to pH 10 with aqueous sodium hydroxide. The mixture is extracted with methylene chloride, dried (MgSO$_4$), and concentrated to give 0.5 g. of the title product as a tan solid. After recrystallization from ethanol, m.p. 188°-189°.

Analysis for: $C_{18}H_{18}N_4O_3.1/2H_2O$; Calculated: C, 62.23; H, 5.51; N, 16.13; Found: C, 62.58; H, 5.38; N, 16.25.

EXAMPLE 6

8-Carbobenzoxy-7,8,9,10-tetrahydro-5H-pyrazino[1,2-a]pyrido[4,3-e]pyrazin-6(6aH)-one To a solution of 2.0 g. of 1-(4-nitro-3-pyridinyl, N-oxide)-4-carbobenzoxypiperazine-2-carboxylic acid, 25 ml. of acetic acid is added, while stirring, 1.5 g. of iron powder. The mixture is warmed to 55° for ½ hour then concentrated. The residue is treated with 10% hydrochloric acid and filtered to give 1.35 g. of the hydrogen chloride salt of the title compound with m.p. 234°-238°. Recrystallization from ethanol-water gives the the title product, m.p. 255°-256° dec.

Analysis for: $C_{18}H_{18}N_4O_3.HCl.1/4H_2O$; Calculated: C, 56.99; H, 5.18; N, 14.77; Found: C, 56.81; H, 5.10; N, 14.50.

EXAMPLE 7

3-Carbobenzoxy-2,3,4,4a-tetrahydro-1H-pyrazino[1,2-a]pyrido[2,3-a]pyrazin-5-(6H)-one To a solution of 4.5 g. of 1-(2-nitro-3-pyridinyl)-4-carbobenzoxypiperazine-2-carboxylic acid in 75 ml. of acetic acid is added, while stirring, 3.0 g. of iron powder. The mixture is heated to 60° for a few minutes then filtered and concentrated. Water is added to the residue and the mixture is extracted with methylene chloride, dried (MgSO$_4$) and concentrated to give 4.5 g. of the title product as a viscous glass. Crystallization from ethanol (Norit) gives 1.8 g., m.p. 190°-192°.

Analysis for: $C_{18}H_{18}N_4O_3$; Calculated: C, 63.89; H, 5.36; N, 16.56; Found: C, 63.64; H, 5.42; N, 16.35.

EXAMPLE 8

8-Carbobenzoxy-2-fluoro-7,8,9,10-tetrahydro-5H-pyrazino[1,2-a]pyrido[3,2-e]pyrazin-6(6aH)-one To a solution of 14.0 g. of 1-(6-fluoro-3-nitro-2-pyridinyl)-4-carbobenzoxypiperazine-2-carboxylic acid in 300 ml. of acetic acid is added, while stirring, 7.0 g. of iron powder. The mixture is warmed to 55° for 3 hours then concentrated. The residue is treated with water and extracted with methylene chloride, dried (MgSO$_4$) and concentrated. The residue is placed on a dry column of alumina and eluted with chloroform. The product band in the column is cut out and the product is washed from the alumina with methanol. Concentration of the methanol wash gives 5.0 g. of the light green-colored title product. Recrystallization from ethanol gives 2.2 g. of pure product, m.p. 210°-214°.

EXAMPLE 9

7,8,9,10-Tetrahydro-5H-pyrazino-[1,2-a]pyrido[3,2-e]pyrazin-6(6aH)-one

A mixture of 1.5 g. of 8-carbobenzoxy-7,8,9,10-tetrahydro-5H-pyrazino[1,2-a]pyrido[3,2-e]pyrazin-6(6aH)-one, 1 g. of 10% palladium on carbon, and 150 ml. of ethanol is hydrogenated at 45 psi for 2 hours. The catalyst is filtered and the filtrate is concentrated. The residue is dissolved in a small amount of ethanol and ethanolic hydrogen chloride is added. Filtration of the precipitated salt gives 0.72 g. of the title product, m.p. 270° dec. Recrystallization from ethanol-water gives 0.60 g., m.p. 278°-279°.

Analysis for: $C_{10}H_{12}N_4O.HCl.H_2O$; Calculated: C, 46.42; H, 5.84; N, 21.65; Found: C, 46.32; H, 5.12; N, 21.42.

EXAMPLE 10

7,8,9,10-Tetrahydro-5H-pyrazino-[1,2-a]pyrido[4,3-e]pyrazin-6(6aH)-one

In a similar procedure to that described in Example 9, from 1.1 g. of 8-carbobenzoxy-7,8,9,10-tetrahydro-5H-pyrazino-[1,2-a]pyrido[4,3-e]pyrazin-6(6aH)-one, there is obtained 0.45 g. of the title product as the hydrochloride salt, m.p. 303°-306°.

Analysis for: $C_{10}H_{12}N_4O.2HCl.1/4H_2O$; Calculated: C, 42.64; H, 5.19; N, 19.89; Found: C, 42.45; H, 5.14; N, 19.87.

EXAMPLE 11

2,3,4,4a-Tetrahydro-5H-pyrazino-[1,2-a]pyrido[2,3-e]pyrazin-5(6H)-one

In a similar procedure to that described in Example 9, from 1.75 g. of 3-carbobenzoxy-2,3,4,4a-tetrahydro-5H-pyrazino-[1,2-a]pyrdio[2,3-e]pyrazin-5(6H)-one, there is obtained 0.55 g. of the title product as the hydrochloride salt, m.p. 315°–319°.

Analysis for: $C_{10}H_{12}N_4O.HCl.1/4H_2O$; Calculated: C, 48.98; H, 5.37; N, 22.85; Found: C, 48.90; H, 5.25; N, 22.79.

EXAMPLE 12

2-Fluoro-7,8,9,10-tetrahydro-5H-pyrazino[1,2-a]pyrido[3,2-e]pyrazin-6(6aH)-one

In a similar procedure to that described in Example 9, from 2.0 g. of 8-carbobenzoxy-2-fluoro-7,8,9,10-tetrahydro-5H-pyrazino[1,2-a]pyrido[3,2-e]pyrazin-6(6aH)-one, there is obtained 0.85 g. of the title product as the hydrochloride salt, m.p. 305°14 308°.

Analysis for: $C_{10}H_{11}H_4OF.HCl.1/4H_2O$; Calculated: C, 45.63; H, 4.79, N, 21.29; Found: C, 45.81; H, 4.75; N, 21.13.

EXAMPLE 13

The antihypertensive effect of a compound of Formula Ia, Ib, or Ic is ellicited and demonstrated by administering the compound to a hypertensive rat and measuring the change in systolic blood pressure 2 and 4 hours after administration. The rats used are either spontaneously hypertensive or are rendered hypertensive by applying a figure-of-eight ligature around one kidney and contralateral nephrectomy. Male spontaneously hypertensive rats derived from the Okamoto-Aoki strain were purchased from commercial breeders. In the renal hypertensive rats, blood pressure tends to stabilize at a hypertensive level after approximately six weeks. A group of at least 4 rats is given the compound by the oral (P.O.) route. Systolic blood pressure, as measured by an indirect technique using the Decker Caudal Plethysmorgraph, is measured prior to administration of the compound and at 2 and 4 hours thereafter. This schedule may vary depending upon the behavior of the compound. A control group of rats, given either a placebo or a standard antihypertensive agent is run with each group of treated rats.

The hypotensive activity of the compound is rated as follows:

| Activity | Systolic Decrease in Blood Pressure | |
|---|---|---|
| Slight | 25 – 35 | mm Hg |
| Moderate | 35 – 50 | |
| Marked | over 50 | |

When tested as described above, the compounds of Formula Ia, Ib, or Ic gave the following results:

| Compound | Activity (P.O.) |
|---|---|
| 7,8,9,10-tetrahydro-5H-pyrazino[1,2-a]pyrido[3,2-e]-pyrazin-6(6aH)-one | Moderate at 2.5 mg/kg |
| 7,8,9,10-tetrahydro-5H-pyrazino[1,2-a]pyrido[4,3-e]-pyrazin-6(6aH)-one | Slight at 20 mg/kg |
| 2,3,4,4a-tetrahydro-1H-pyrazino[1,2-a]pyrido[2,3-e]-pyrazin-5(6H)-one | Marked at 25 mg/kg |
| 2-fluoro-7,8,9,10-tetrahydro-5H-pyrazino[1,2-a]pyrido[3,2-e]pyrazin-6(6aH)-one | Marked at 20 mg/kg |

What is claimed is:
1. A compound of the formula:

wherein:
R is hydrogen, chlorine, or fluorine; and
$R^1$ is hydrogen, methyl, ethyl, propyl, or isopropyl, or a non-toxic pharmaceutically acceptable acid addition salt thereof.

2. The compound as defined in claim 1 which is 7,8,9,10-tetrahydro-5H-pyrazino[1,2-a]pyrido[3,2-e]pyrazin-6(6aH)-one.

3. The compound as defined in claim 1 which is 2-fluoro-7,8,9,10-tetrahydro-5H-pyrazino[1,2-a]pyrido[3,2-e]pyrazin-6(6aH)-one.

4. The compound as defined in claim 1 which is 8-carbobenzoxy-7,8,9,10-tetrahydro-5H-pyrazino[1,2-a]pyrido[3,2-e]-pyrazino-6(6aH)-one.

5. The compound as defined in claim 1 which is 8-carbobenzoxy-2-fluoro-7,8,9,10-tetrahydro-5H-pyrazino[1,2-a]-pyrido[3,2-e]pyrazin-6(6aH)-one.

6. A compound of the formula:

wherein
$Y^1$ is carbobenzoxy, benzhydryl, benzyl, trifluoroacetyl, t-butyloxy carbonyl, or tosyl; and
R is hydrogen, chlorine, or fluorine.

* * * * *